United States Patent [19]

Berka et al.

[11] Patent Number: 5,219,753
[45] Date of Patent: Jun. 15, 1993

[54] **GENETICALLY ENGINEERED MICROORGANISMS CONTAINING A GENE SEGMENT CODING FOR A LIPASE FROM *RHIZOPUS DELEMAR***

[75] Inventors: Thomas R. Berka, Wyncote; Michael J. Haas, Glenside, both of Pa.

[73] Assignee: The United States of America as represented by the Secretary of Agriculture, Washington, D.C.

[21] Appl. No.: 369,975

[22] Filed: Jun. 22, 1989

[51] Int. Cl.⁵ .............. C12N 15/00; C12N 15/55; C12N 15/70

[52] U.S. Cl. ................. 435/252.3; 435/198; 435/252.33; 435/320.1; 935/14; 935/31; 935/29; 935/73; 536/23.2

[58] Field of Search ........... 435/69.1, 171.1, 320.1, 435/252.3, 198, 252.33; 536/27

[56] References Cited

U.S. PATENT DOCUMENTS 5,041,378  8/1991  Drummond et al. ............... 435/234

FOREIGN PATENT DOCUMENTS 1-080290  3/1989  Japan .

OTHER PUBLICATIONS

Chiba, et al., Biochem. Biophys. Acta, vol. 327, (1973), pp. 380–392.
Mohsen, et al., Egypt J. Food Sci., vol. 14, No. 1, (1986), pp. 147–156.
Boel, et al., Lipids, vol. 23, No. 7, (1988), pp. 701–706.
Hanna, et al., Gene, vol. 30, (1984), pp. 247–250.
Young, et al., Proc. Natl. Acad. Sci. (USA), vol. 80, (1983), pp. 1194–1198.
Kouker, et al., Appl. Environ. Micro., Jan. 1987, pp. 211–213.
Rosenberg, Martin et al., "The Use of pKC30 and Its Derivatives for Controlled Expression of Genes", *Methods in Enzymology*, vol. 101, pp. 123–138.
Guarente, Leonard, "Yeast Promoters and lacZ Fusions Designed to Study Expression of Cloned Genes in Yeast", *Methods in Enzymology*, vol. 101, pp. 181–191.
Ammerer, Gustav, "Expression of Genes in Yeast Using the ADCI Promoter", *Methods in Enzymology*, vol. 101, pp. 191–201.
Beier, David R., et al., "Characterization of a Regulatory Region Upstream of the ADR2 locus of *S. Cerevisiae*", *Nature*, vol. 300, 23–30 Dec. 1982, pp. 724–727.
Rogers, S. G., et al., "Improved Vectors for Plant Transformation: Expression Cassette Vectors and New Selectable Markers", *Methods in Enzymology*, vol. 153, pp. 253–277.
Remaut, Erik, et al., "Expression of Heterologous Unfused Protein in *Escherichia coli*, *Methods in Enzymology*", vol. 153, pp. 416–431.
Duffaud, Guy D., et al., "Expression and Secretion of Foreign Proteins in *Escherichia coli*", *Methods in Enzymology*, vol. 153, pp. 492–507.
Chang, Shing, "Engineering for Protein Secretion in Gram-Positive Bacteria", *Methods in Enzymology*, vol. 153, pp. 507–517.
Piccini, Antonia, et al., "Vaccinia Virus as an Expression Vector", *Methods in Enzymology*, vol. 154, pp. 3–28.
Okayama, H., et al., "High-Efficiency Cloning of Full-Length cDNA; Construction and Screening of cDNA Expression Libraries for Mammalian Cells", *Methods in Enzymology*, vol. 154, pp. 3–28.
Molecular Cloning, A Laboratory Manual, 2nd Edition, J. Sambrook et al., Cold Spring Harbor Laboratory Press, 1989, "Expression of Cloned Genes in *Escherichia coli*", pp. 17.3–17.44.

(List continued on next page.)

*Primary Examiner*—Robert A. Wax
*Assistant Examiner*—William W. Moon
*Attorney, Agent, or Firm*—M. Howard Silverstein; Randall E. Deck; John D. Fado

[57] ABSTRACT

A lipase purified from *Rhizopus delemar* can be produced by cultivating a genetically engineered host microorganism transformed with a gene coding for the lipase. Additionally disclosed is a method for the detection or screening for production of lipase by genetically engineered organisms.

18 Claims, 3 Drawing Sheets

Restriction Map of pUC8.2-14

OTHER PUBLICATIONS

Molecular Cloning, A Labatory Manual, 2nd Edition, J. Sambrook et al., Cold Spring Harbor Laboratory Press, 1989, "Expression of Cloned Genes in Cultured Mammalian Cells", pp. 16.2–16.81.

*Genes,* Benjamin Lewin, Editor, Cell, Chapter 19, "Dealing with DNA", 1982, pp. 300–311.

Spoerel, Nikolaus, et al., "Identification of Genomic Sequences Corresponding to cDNA Clones, *Methods in Enzymology*", vol. 152, pp. 588–597.

Beltz, Gerald A., et al., "Isolation of Multigene Families and Determination of Homologies by Filter Hybridization Methods", *Methods in Enzymology,* vol. 100, pp. 266–285.

Grunstein, Michael, et al., "Colony Hybridization: A Method for the Isolation of Cloned DNAs that Contain a Specific Gene", *Proc. Nat. Acad. Sci.,* USA 72 (1975), vol. 72, No. 10, pp. 3961–3965.

Benton, W. David, et al., "Screening Δgt Recombinant Clones by Hybridization to Single Plaques in situ", Abstract, *Science,* vol. 196, pp. 180–182.

Hanahan, Douglas, et al., "Plasmid Screening at High Colony Density", Gene, 10 (1980), Elsevier/North-Holland Biomedical Press, pp. 63–67.

Errington, Jeff, "Generalized Cloning Vectors for *Bacillus subtilis*", *Vectors A Survey of Melecular Cloning Vectors and Their Uses,* pp. 345–362.

*Cloning Vectors A Laboratory Manual,* Pouwels, P. H., et al., Elsevier Science Publishers B.V., 1985, "Vectors for Gram-positive Bacteria (Bacillus), General purpose cloning vectors", pp. IV–1, IV–3, IV–A–a–i--l–IV–B–a–ii–l, IV–7, IV–9, IV–11, IV–13, V–5.

Iwai M. and Tsujisaka, Y., 1974, Agricultural and Biological Chemistry 38(6): 1241–1247.

*Molecular Cloning A Laboratory Manual,* Maniatis, T., et al., Cold Spring Harbor Laboratory, 1982, "The Identifiction of Recombinant Clones", pp. 310–328.

Lane:

1  2

Restriction Map of pUC8.2-14

GENETICALLY ENGINEERED MICROORGANISMS CONTAINING A GENE SEGMENT CODING FOR A LIPASE FROM *RHIZOPUS DELEMAR*

BACKGROUND OF THE INVENTION

1. Field of the Invention

Lipases (glycerol ester hydrolases EC 3.1.1.3) are enzymes which hydrolyze the glycerol esters of long chain fatty acids (glycerides).

This invention relates to the production of a lipase from *Rhizopus delemar* (*R. delemar*) using recombinant DNA (deoxyribonucleic acid) methods. The lipase coding gene from *R. delemar* is inserted into host microorganisms for the production of lipase products.

The uses of lipases to exchange glyceride fatty acids with free fatty acids or those of other glycerides and for the conduct of a range of chemical reactions in organic solvents have been described. Lipases can also be used to release fatty acids from glycerides.

Commercially, fatty acids are important chemicals used in a variety of consumer goods including cosmetics, foods, plastics, paints, varnishes, lubricating greases and household cleaners. The major sources of fatty acids are fats and oils from animals and plants. Fats and oils are composed of triglycerides, that can be subsequently broken down to free fatty acids and glycerol. Free fatty acids have been traditionally prepared by chemical hydrolysis using both high temperature and pressure. An alternative to chemical hydrolysis is an enzymatic process using lipases.

Enzymatic hydrolysis of triglycerides has the advantage of a reaction environment at reduced temperature and pressure. Lipase, although overcoming the disadvantages of chemical hydrolysis, does not completely split the triglyceride molecule. The disadvantage, however, of this enzymatic hydrolysis is that it necessitates use of considerable amounts of a very expensive enzyme. As such, there is a need for the production of an inexpensive lipase available in quantity.

Molecular cloning and expression of a lipase gene offers a method to address this need. In addition, the availability of a cloned lipase gene facilitates the use of site directed mutagenic techniques to modify lipase so as to improve its utility.

2. Description of the Prior Art

Lipase cDNA has been cloned and sequenced from a similar fungus *Rhizomucor miehei*. Sequenced inserts from *E. coli* yielded a probable amino acid sequence of the extracellular lipase secreted by that organism. While sequence information was obtained there was no expression by the transformed host, Boel, et. al., Lipids, Vol. 23, No. 7, (1988), p. 701. The sequence of the cDNA from *R. miehei* is not identical to that reported here.

Lipases from *R. delemar* have been purified to varying degrees, Chiba, et al., Biochem. Biophys. Acta, Vol. 327, (1973), p. 380; Fukumoto, et al., J. Gen. Appl. Microbiol., Vol. 10, No. 3, (1964), p. 257; Iwai and Tsujisaka, Agr. Biol. Chem., Vol. 38, (1974), p. 1241; Mohsen, et al., Egypt. J. Food Sci., Vol. 14, No. 1, (1986), p. 147. In none of these reports is the lipase demonstrated to be free of contaminating non-lipase proteins.

It has recently been determined that a partially purified sample of crude *R. delemar* lipase contained at least 10 different proteins, Antonian, Lipids, Vol. 23, No. 12, (1988), p. 1101. Due to the discrepancies in the literature, it is apparent that prior to the instant invention, no single lipase from *R. delemar* has been purified to homogeneity.

Kouker and Jaeger [Appl. Environ. Microbiol., Vol. 51, (1987), p. 211] have described a method employing medias containing Rhodamine B and olive oil for the detection of naturally occurring organisms which produce lipase. However, no such method has been described for the screening of organisms containing recombinant DNAs.

SUMMARY OF THE INVENTION

The present invention is directed to purified *R. delemar* lipase, to recombinant DNA molecules having a cDNA copy of the gene encoding a lipase from *Rhizopus delemar* and having the nucleic acid sequence shown in Table 1, to the lipase produced in cells containing these recombinant DNA molecules, and to a method for the detection of organisms containing recombinant DNAs which direct lipase production. Based on the cloning protocol and vector employed here the upper of the two DNA strands displayed in Table 1 can be identified as analogous to the mRNA for lipase. On the basis of the known amino terminal sequence of the purified fungal lipase, the mature protein begins at base pair (b.p.) 415 in the cDNA sequence.

Poly A enriched RNA was isolated from *R. delemar*, cDNA was synthesized using this RNA as template. A selected vector was cut with an appropriate restriction enzyme, ligated via conventional techniques to the ends of the fragments of *R. delemar* cDNA, and inserted into a host microorganism resulting in the synthesis of an active lipase. The predicted protein amino acid sequence, from amino to carboxy terminus, encoded by the insert and derived from the data of Table 1, as shown in Table 2.

TABLE 1

|     | 3 | | 9 | | 15 | | 21 | | 27 | | 33 | | 39 | | 45 |
| --- | --- | --- | --- | --- | --- | --- | --- | --- | --- | --- | --- | --- | --- | --- | --- |
| 1 | GAA | TTC | CCT | TTT | CTT | CTT | ACC | CCT | TCC | AGT | TCT | TTA | CTA | TCA | ATC |
|   | CTT | AAG | GGA | AAA | GAA | GAA | TGG | GGA | AGG | TCA | AGA | AAT | GAT | AGT | TAG |
| 46 | ATG | GTT | TCA | TTC | ATT | TCC | ATT | TCT | CAA | GGT | GTT | AGT | CTT | TGT | CTT |
|   | TAC | CAA | AGT | AAG | TAA | AGG | TAA | AGA | GTT | CCA | CAA | TCA | GAA | ACA | GAA |
| 91 | CTT | GTC | TCT | TCC | ATG | ATG | CTC | GGT | TCA | TCT | GCT | GTT | CCT | GTT | TCT |
|   | GAA | CAG | AGA | AGG | TAC | TAC | GAG | CCA | AGT | AGA | CGA | CAA | GGA | CAA | AGA |
| 136 | GGT | AAA | TCT | GGA | TCT | TCC | AAC | ACC | GCC | GTC | TCT | GCA | TCT | GAC | AAT |
|   | CCA | TTT | AGA | CCT | AGA | AGG | TTG | TGG | CGG | CAG | AGA | CGT | AGA | CTG | TTA |
| 181 | GCT | GCC | CTC | CCT | CCT | CTC | ATC | TCC | AGC | CGT | TGT | GCT | CCT | CCT | TCT |
|   | CGA | CGG | GAG | GGA | GGA | GAG | TAG | AGG | TCG | GCA | ACA | CGA | GGA | GGA | AGA |
| 226 | AAC | AAG | GGA | AGT | AAA | AGC | GAT | CTC | CAA | GCT | GAA | CCT | TAC | AAC | ATG |

TABLE 1-continued

```
    TTG TTC CCT TCA TTT TCG CTA GAG GTT CGA CTT GGA ATG TTG TAC

271 CAA AAG AAT ACA GAA TGG TAT GAG TCC CAT GGT GGC AAC CTG ACA
    GTT TTC TTA TGT CTT ACC ATA CTC AGG GTA CCA CCG TTG GAC TGT

316 TCC ATC GGA AAG CGT GAT GAC AAC TTG GTT GGT GGC ATG ACT TTG
    AGG TAG CCT TTC GCA CTA CTG TTG AAC CAA CCA CCG TAC TGA AAC

361 GAC TTA CCC AGC GAT GCT CCT CCT ATC AGC CTC TCT AGC TCT ACC
    CTG AAT GGG TCG CTA CGA GGA GGA TAG TCG AGA GAT CGA GAT GG
```

↓ START OF MATURE FUNGAL PROTEIN

```
406 AAC AGC GCC TCT GAT GGT GGT AAG GTT GTT GCT GCT ACT ACT GCT
    TTG TCG CGG AGA CTA CCA CCA TTC CAA CAA CGA CGA TGA TGA CGA

451 CAG ATC CAA GAG TTC ACC AAG TAT GCT GGT ATC GCT GCC ACT GCC
    GTC TAG GTT CTC AAG TGG TTC ATA CGA CCA TAG CGA CGG TGA CGG

496 TAC TGT CGT TCT GTT GTC CCT GGT AAC AAG TGG GAT TGT GTC CAA
    ATG ACA GCA AGA CAA CAG GGA CCA TTG TTC ACC CTA ACA CAG GTT

541 TGT CAA AAG TGG GTT CCT GAT GGC AAG ATC ATC ACT ACC TTT ACC
    ACA GTT TTC ACC CAA GGA CTA CCG TTG TAG TAG TGA TGG AAA TGG

586 TCC TTG CTT TCC GAT ACA AAT GGT TAC GTC TTG AGA AGT GAT AAA
    AGG AAC GAA AGG CTA TGT TTA CCA ATG CAG AAC TCT TCA CTA TTT

631 CAA AAG ACC ATT TAT CTT GTT TTC CGT GGT ACC AAC TCC TTC AGA
    GTT TTC TGG TAA ATA GAA CAA AAG GCA CCA TGG TTG AGG AAG TCT

676 AGT GCC ATC ACT GAT ATC GTC TTC AAC TTT TCT GAC TAC AAG CCT
    TCA CGG TAG TGA CTA TAG CAG AAG TTG AAA AGA CTG ATG TTC GGA

721 GTC AAG GGC GCC AAA GTT CAT GCT GGT TTC CTT TCC TCT TAT GAG
    CAG TTC CCG CGG TTT CAA GTA CGA CCA AAG GAA AGG AGA ATA CTC

766 CAA GTT GTC AAT GAC TAT TTC CCT GTC GTC CAA GAA CAA TTG ACC
    GTT CAA CAG TTA CTG ATA AAG GGA CAG CAG GTT CTT GTT AAC TGG

811 GCC CAC CCT ACT TAT AAG GTC ATC GTT ACC GGT CAC TCA CTC GGT
    CGG GTG GGA TGA ATA TTC CAG TAG CAA TGG CCA GTG AGT GAG CCA

856 GGT GCA CAA GCT TTG CTT GCC GGT ATG GAT CTC TAC CAA CGT GAA
    CCA CGT GTT CGA AAC GAA CGG CCA TAC CTA GAG ATG GTT GCA CTT

901 CCA AGA TTG TCT CCC AAG AAT TTG AGC ATC TTC ACT GTC GGT GGT
    GGT TCT AAC AGA GGG TTC TTA AAC TCG TAG AAG TGA CAG CCA CCA

946 CCT CGT GTT GGT AAC CCC ACC TTT GCT TAC TAT GTT GAA TCC ACC
    GGA GCA CAA CCA TTG GGG TGG AAA CGA ATG ATA CAA CTT AGG TGG

991 GGT ATC CCT TTC CAA CGT ACC GTT CAC AAG AGA GAT ATC GTT CCT
    CCA TAG GGA AAG GTT GCA TGG CAA GTG TTC TCT CTA TAG CAA GGA

1036 CAC GTT CCT CCT CAA TCC TTC GGA TTC CTT CAT CCC GGT GTT GAA
     GTG CAA GGA GGA GTT AGG AAG CCT AAG GAA GTA GGG CCA CAA CTT

1081 TCT TGG ATC AAG TCT GGT ACT TCC AAC GTT CAA ATC TGT ACT TCT
     AGA ACC TAG TTC AGA CCA TGA AGG TTG CAA GTT TAG ACA TGA AGA

1126 GAA ATT GAA ACC AAG GAT TGC AGT AAC TCT ATC GTT CCT TTC ACC
     CTT TAA CTT TGG TTC CTA ACG TCA TTG AGA TAG CAA GGA AAG TGG

1171 TCT ATC CTT GAC CAC TTG AGT TAC TTT GAT ATC AAC GAA GGA AGC
     AGA TAG GAA CTG GTG AAC TCA ATG AAA CTA TAG TTG CTT CCT TCG

1216 TGT TTG TAA AAC ACT TGA CGT GTT ACT CTA ATT TTA TAA TAA AAT
     ACA AAC ATT TTG TGA ACT GCA CAA TGA GAT TAA AAT ATT ATT TTA

1261 TAA GTT TTT ATA CAA TAA AAG GAA TTC
     ATT CAA AAA TAT GTT ATT TTC CTT AAG
```

TABLE 2

```
              5              10              15              20              25              30
 1  M  V  S  F  I  S  I  S  Q  G  V  S  L  C  L  L  V  S  S  M  M  L  G  S  S  A  V  P  V  S
31  G  K  S  G  S  S  N  T  A  V  S  A  S  D  N  A  A  L  P  P  L  I  S  S  R  C  A  P  P  S
61  N  K  G  S  K  S  D  L  Q  A  E  P  Y  N  M  Q  K  N  T  E  W  Y  E  S  H  G  G  N  L  T
91  S  I  G  K  R  D  D  N  L  V  G  G  M  T  L  D  L  P  S  D  A  P  P  I  S  L  S  S  S  T
```

TABLE 2-continued

| 121 | N | S | A | S | D | G | G | K | V | V | A | A | T | T | A | Q | I | Q | E | F | T | K | Y | A | G | I | A | A | T | A |
| --- | - | - | - | - | - | - | - | - | - | - | - | - | - | - | - | - | - | - | - | - | - | - | - | - | - | - | - | - | - | - |
| 151 | Y | C | R | S | V | V | P | G | N | K | W | D | C | V | Q | C | Q | K | W | V | P | D | G | K | I | I | T | T | F | T |
| 181 | S | L | L | S | D | T | N | G | Y | V | L | R | S | D | K | Q | K | T | I | Y | L | V | F | R | G | T | N | S | F | R |
| 211 | S | A | I | T | D | I | V | F | N | F | S | D | Y | K | P | V | K | G | A | K | V | H | A | G | F | L | S | S | Y | E |
| 241 | Q | V | V | N | D | Y | F | P | V | V | Q | E | Q | L | T | A | H | P | T | Y | K | V | I | V | T | G | H | S | L | G |
| 271 | G | A | Q | A | L | L | A | G | M | D | L | Y | Q | R | E | P | R | L | S | P | K | N | L | S | I | F | T | V | G | G |
| 301 | P | R | V | G | N | P | T | F | A | Y | Y | V | E | S | T | G | I | P | F | Q | R | T | V | H | K | R | D | I | V | P |
| 331 | H | V | P | P | Q | S | F | G | F | L | H | P | G | V | E | S | W | I | K | S | G | T | S | N | V | Q | I | C | T | S |
| 361 | E | I | E | T | K | D | C | S | N | S | I | V | P | F | T | S | I | L | D | H | L | S | Y | F | D | I | N | E | G | S |
| 391 | C | L | | | | | | | | | | | | | | | | | | | | | | | | | | | | |

An extracellular lipase from *R. delemar* was purified essentially to homogeneity. Comparison of the amino acid sequence of its first 28 amino terminal residues showed 100% homology with the predicted amino acid sequence derived from the cloned cDNA beginning at nucleotide 415 (Table 1). This indicates that the cloned cDNA corresponds to the gene found in *R. delemar* coding for native lipase. In conjunction with these experiments we have developed and applied a novel method for the detection of organisms containing recombinant DNA molecules which direct the synthesis of lipolytic enzymes.

DETAILED DESCRIPTION OF THE INVENTION

Purification of Lipase from *Rhizopus delemar*

EXAMPLE 1

1) *Rhizopus delemar* ATCC 34612 was obtained from the American Type Culture Collection, 12301 Parklawn Drive, Rockville, Md. 20852, USA and cultured in a liquid media containing inorganic salts, 30 mM glycerol, 0.5% casein hydrolyzate and $5 \times 10^{-7}$% biotin while shaken at 30° C. for about 36 hours. The media was filtered using cheesecloth. To the filtrate was added sodium azide, pepstatin, EDTA, leupeptin and phenylmethylsufonyl fluoride. This final solution was used as the "crude lipase."

2) An affinity chromatography resin was prepared by attaching oleic acid to a solid support. Crude lipase was applied. The column was washed 10 mM sodium phosphate pH 6.0, and with this buffer containing 5% sodium chloride. Lipase was then eluted by application of a gradient of non-ionic detergent (Triton X-100) in 10 mM sodium phosphate, pH 6.0. The eluted lipase was detected by a titrimetric method monitoring the enzyme dependent release of fatty acids from olive oil.

3) Lipase containing fractions were collected and applied to a column containing a cation exchange resin. The column was washed with 10 mM sodium phosphate buffer, pH 6.0. Proteins were eluted by a linear gradient of NaCl from 0 to 0.5M in the wash buffer. Fractions were assayed for lipase activity titrimetrically as above. The fraction containing the lipase activity was analyzed electrophoretically by SDS polyacrylamide gel electrophoresis. Protein bands were detected by conventional silver stain techniques.

Figure 1:
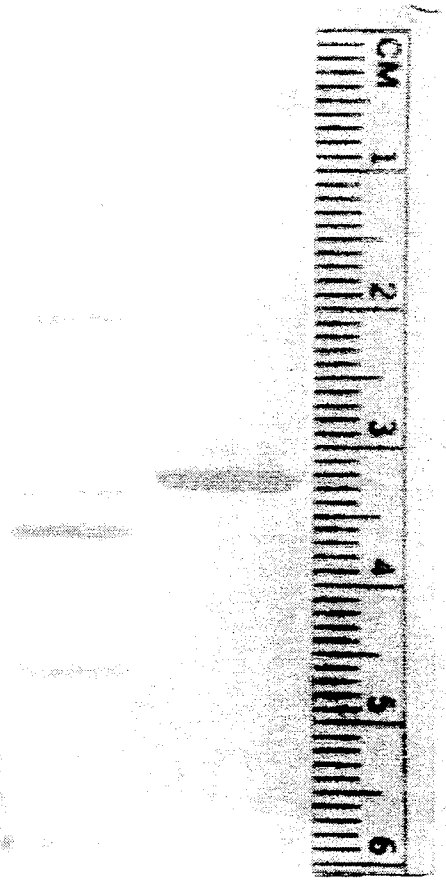
FIG. 1 is a photograph of a sodium dodecyl sulfate (SDS) polyacrylamide gel. Lane 1 contains control molecular weight marker proteins with molecular masses of 66,000, 45,000, 36,000, 29,000, 24,000, 20,100, and 14,200 daltons. Lane 2 shows the essentially homogeneous band resulting from the application of three micrograms of purified lipase obtained from the ion exchange chromatography step.

The active lipase peak contained but a single protein species as detected on SDS-acrylamide electrophoresis gels (FIG. 1). The molecular mass of this species is calculated from the gel to be about 30,261.

Figure 2:
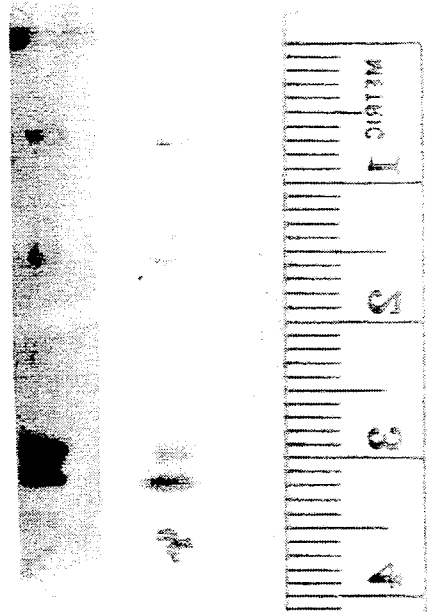
FIG. 2 is a photograph of two portions of an isoelectric focusing gel to which were applied samples of the purified active lipase. The left pattern was stained with silver stain and shows the pure protein preparation to contain two entities. The right pattern is an analogous sample stained with an activity stain specific for esterases. These data indicate that the purified protein contains two isozyme forms, each of which is an esterase, of which lipases are a type.

On isoelectric focusing this preparation is shown to contain two protein species both of which possess esterolytic activity (FIG. 2). This demonstrates that the predominant proteins of the purified preparation are lipases. We have determined the isoelectric points of these species to be approximately 8.05.

The amino acid composition of this species is presented in Table 3. This composition is significantly different from that previously reported for a *R. delemar* lipase (Table 3).

The sequence of the first 28 amino terminal residues of this protein is presented in Table 4. The ability to determine the amino acid sequence over this relatively long stretch supports the conclusion that the purified lipase is essentially homogenous, with no more than minor sequence differences between the two isozyme forms which can be separated by isoelectric focusing.

EXAMPLE 2

Isolation of *R. delemar* poly (A+) RNA

*R. delemar* mRNA was prepared in the manner of Chirgwin, et al., Biochemistry, Vol. 18, (1979), p. 5294 and Maniatis, et al., Molecular Cloning: A Laboratory Manual, Cold Spring Harbor Laboratory, (1982), Cold Spring Harbor, N.Y. Poly (A)+RNA was enriched by affinity chromatography using an oligo (dT) cellulose support and described by Aviv, et al., Proc. Nat. Acad. Sci., Vol. 69, (1972), p. 1408.

TABLE 3

Lipase Amino Acid Compositions

| Amino Acid | Letter Designation | Chiba, et al.* | Predicted** by Gene INV. | Purified Lipase |
| --- | --- | --- | --- | --- |
| Alanine | A | 25 | 15 | 19 |
| Arginine | R | 13 | 9 | 10 |
| Asparagine | N | | 10 | |
| (ASX) | | (30) | | (28) |
| Aspartic Acid | D | | 13 | |
| Cysteine | C | 6 | 6 | 8 |
| Glutamine | Q | | 13 | |

TABLE 3-continued

| | Lipase Amino Acid Compositions | | | |
|---|---|---|---|---|
| Amino Acid | Letter Designation | Chiba, et al.* | Predicted** by Gene INV. | Purified Lipase |
| (GLX) | | (45) | | (24) |
| Glutamic Acid | E | | 9 | |
| Glycine | G | 9 | 21 | 21 |
| Histidine | H | 9 | 7 | 8 |
| Isoleucine | I | 8 | 17 | 14 |
| Leucine | L | 33 | 16 | 17 |
| Lysine | K | 33 | 15 | 18 |
| Methionine | M | 2 | 1 | 2 |
| Phenylalanine | F | 15 | 15 | 14 |
| Proline | P | 17 | 15 | 16 |
| Serine | S | 15 | 24 | 22 |
| Threonine | T | 19 | 22 | 21 |
| Tryptophan | W | 8 | 3 | N.D. |
| Tyrosine | Y | 30 | 12 | 11 |
| Valine | V | 22 | 26 | 19 |

*Chiba, et al., Biochem. Acta., Vol. 327, (1973), p. 380, predicted protein size of 390 amino acid residues.
**Predicted protein size of 269 amino acid residues from gene invention.
N.D. = Not determined.

TABLE 4

Amino Acid Sequence of First 28 Amino Terminal Residues of Purified R. delemar Lipase

NH$_2$—S—D—G—G—K—V—V—A—A—T—T—A—Q—I—Q—E—F—

T—K—Y—A—G—I—A—A—T—A—Y—COOH

EXAMPLE 3

First Strand cDNA Synthesis

1) To a sterile diethylpyrocarbonate (DEPC)-treated microcentrifuge tube on ice was added:
 a) 10 μl 5X first strand buffer (250 mM Tris-HCl pH 8.3, 375 mM KCl, 15 mM MgCl, 50 mM dithiothreitol);
 b) 2.5 μl 10 mM dNTP mix (10 mM dATP, 10 mM DCTP, 10 mM dGTP, 10 mM dTTP);
 c) 5 μl Oligo (dT)$_{12-18}$ (0.5 mg/ml);
 d) 8 μg polyA+RNA from *Rhizopus delemar*; and
 e) DEPC-treated water to a volume of 47.5 μl.

2) Initiated first strand synthesis reaction by adding 2.5 μl of M-MLV Reverse Transcriptase (200 μ/μl). Mix.

3) Immediately transferred 10 μl to a separate DEPC-treated microcentrifuge tube containing 1 μCi [α$^{32}$P] dCTP (3000 Ci/mmol) as tracer nucleotide to monitor synthesis.

4) Incubated both reaction tubes (10 μl tracer reaction of Step 3 and the remaining 40 μl from Step 2) at 37° C. for 1 hr, then placed on ice.

5) Terminated the 10 μl tracer reaction with 1 μl of 0.25M Na$_2$ EDTA, pH 7.5 while still on ice.

6) The 40 μl reaction mixture was then used in the procedure for second cDNA strand synthesis (EXAMPLE 4).

7) To the terminated tracer reaction was added 89 μl of DEPC-treated water and duplicate 5 μl samples were spotted on glass fiber filters.

8) One of the spotted filters was allowed to dry at room temperature. The other filter was washed sequentially 3×with ice-cold 10% (w/v) trichloroacetic acid (TCA) containing 1% (w/v) sodium pyrophosphate at 50 ml per wash for 5 minutes (min) each wash. Then the filter was washed (1×) using 50 ml of 95% ethanol (ETOH) at room temperature for 5 min. The filter was then dried under a heat lamp.

9) Both filters were then counted to determine the amount of $^{32}$P in the reaction mixture as well as the amount incorporated into the first cDNA strand using conventional scintillation techniques.

10) The remaining 90 μl of tracer reaction was extracted with phenol and then ethanol-precipitated by conventional method steps.

EXAMPLE 4

Second Strand cDNA Synthesis

1) To the 40 μl of reaction mixture obtained from EXAMPLE 3 was added:
 a) 231.6 μl DEPC-treated water;
 b) 6 μl of 10 mM dNTP mix (as described in EXAMPLE 3);
 c) 32 μl of 10X second strand buffer (188 mM Tris-HCl, pH 8.3, 906 KCl, 46 mM MgCl$_2$, 37.5 mM DTT);
 d) 1 ul (α$^{32}$P) dCTP (10 μCi/μl, 3000/Ci/mmol);
 e) 8 ul *E. coli* DNA Polymerase I (10 U/μl);
 f) 1.4 ul *E. coli* RNase H (2 U/μl).

2) The reaction tube was mixed gently by vortexing and incubated for 2 hr at 15° C.

3) The reaction tube was then placed on ice and the reaction terminated by adding 25 ul of 0.25M Na$_2$EDTA (pH 7.5), thus forming the second strand mixture.

4) 10 ul of the second strand mixture was added to 90 μl of DEPC-treated water. A 5 μl aliquot of this mixture was spotted onto a glass fiber filter and allowed to dry at room temperature.

5) Removed a 10 μl aliquot from the second strand mixture and spotted onto another glass fiber filter. This filter was then washed sequentially 3×with ice cold 10% (w/v) TCA containing 1% (w/v) sodium pyrophosphate at 50 ml per wash for 5 min each. Then the filter was washed once with 50 ml of 95% ethanol at room temperature for 5 min and dried under a heat lamp.

6) The filters were counted by scintillation techniques to determine the amount of $^{32}$P in the reaction mixture as well as the amount of $^{32}$P incorporated.

7) The remaining second strand mixture was extracted with phenol and precipitated with ethanol by conventional method steps.

8) The precipitate from 7 was dissolved in 200 μl of sterile 10 mM Tris-HCl, pH 7.4, 1 mM Na$_2$EDTA (TE) buffer and reprecipitated using ammonium acetate and ethanol by conventional method steps and dried under vacuum in a microcentrifuge.

9) The dried pellet was dissolved in 20 μl of sterile TE buffer. A 2 μl aliquot of this solution was saved for gel analysis.

EXAMPLE 5 cDNA Linker Addition

Linker addition was accomplished using well known techniques described in Basic Methods in Molecular Biology, Davis, L. G. et al., (1986), New York, Elsevier Scientific Press and Maniatis, et al., Ibid., and herein incorporated by reference. It is envisioned that the cDNA for a lipase from *R. delemar* can be linked using any known linker for insertion into a vector in the proper reading frame in order to express product.

The cDNA was first methylated using Eco RI methylase and S-adenosylmethionine to protect putative internal Eco RI sites. The cDNA molecules were then incubated with T4 DNA polymerase. The cDNA molecules were blunt ended with T4 DNA polymerase to ensure all the ends were filled in and flush.

The cDNA was then ligated with Eco RI linker molecules using standard linker ligation procedures. Multiples of annealed linkers were eliminated by digestion with Eco RI endonuclease. Additional purification of the linked cDNA from excess linker molecules was achieved by electrophoresing the linkered cDNA in a 5% (w/v) polyacrylamide gel, excising the region of the gel containing the cDNA, and then electroeluting the cDNA from the gel using standard conventional methods.

EXAMPLE 6

Insertion of Lipase cDNA Into Bacteriophage λgt11

*E. coli* genotype ΔlacU169 pro A+Δlon ara D139 strA hflA [chr::Tn10] hsd R−hsd M+(pMC9) designated as strain Y1089 (r−) and *E. coli* genotype ΔlacU169 proA+Δlon araD139 strA supF [trpC22::Tn10] hsd R−hsd M+(pMC9) designated as strain Y1090 (r−) and bacteriophage λgt11 DNA, described by Young, et al., Proc. Natl. Acad. Sci., U.S.A., Vol. 80, (March 1983), p. 1194 were obtained from Promega Biotec (Madison).

1) The cDNA bounded by Eco RI linkers from EXAMPLE 5 was ligated to commercially available Eco RI-digested, phosphatased-treated arms of DNA of the bacteriophage λgt11 cloning and expression vector (Promega Biotec, Madison) using standard techniques.

2) The recombinant λgt11 DNA molecules were then packaged in vitro to form infective particles using a commercially available in vitro lambda DNA packaging system (Promega Biotec, Madison) and following standard in vitro packaging techniques. The packagedrecombinant λgt11 molecules constituted a *R. delemar* cDNA library. The titer of the phage in the library was determined by standard methods and using *E. coli* Y1090r−(Promega Biotec, Madison) as the indicator bacteria.

3) Using *E. coli* Y1090r− as the indicator bacteria, the library was then plated by standard techniques to give individual plaques on the lipase screening agar medium described in Table 5 (a), with the exception that isopropyl-β-D-thiogalactopyranoside (IPTG) was omitted from the bottom and top agar. After incubating for approximately 3.5 hr at 37°, the plates were sprayed with a 10 mM solution of IPTG to induce lipase expression. In another embodiment the IPTG can be incorporated into the lipase screening agar as per Table 5. A bacteriophage recovered from one of the plaques exhibiting lipase activity was recovered and designated R45A4.

4) Additionally, phage R45A4 was used to lysogenized *E. coli* Y1089 (r−), a commercially available high frequency lysogenization strain (Promega Biotec, Madison). The lysogen *E. coli* Y1089r−(R45A4) was selected on lipase screening medium (Table 5) and identified as a fluorescent orange colony when viewed under ultraviolet illumination. Plaques that fluoresced orange under UV were picked and the phage purified.

The phage designated R45A4 contained a novel Eco RI restriction fragment approximately 1287 b.p. in length. Lipase produced by this lysogen was shown to possess the 1,3 positioned specificity exhibited by the lipase produced by *R. delemar* using thin layer chromatography.

TABLE 5

| (a) | Wt./liter Lipase Screening Agar Composition |
|---|---|
| Tryptone | 10 g. |
| Yeast Extract | 5 g. |
| NaCl | 5 g. |
| Olive Oil | (1% vol./vol.) |
| Rodamine B Solution | 10 ml (0.001% wt./vol.) |
| Agar | (1.5–2.0% wt./vol.; 0.6% wt./vol.) for top agar for plating phage) |
| pH adjusted to 7.5 with NaOH | |
| (b) | Luria-Bertani Medium |
| Tryptone | 10 g. |
| Yeast Extract | 5 g. |
| NaCl | 5 g. |
| pH adjusted to 7.5 with NaOH | |

EXAMPLE 7

Figure 3:
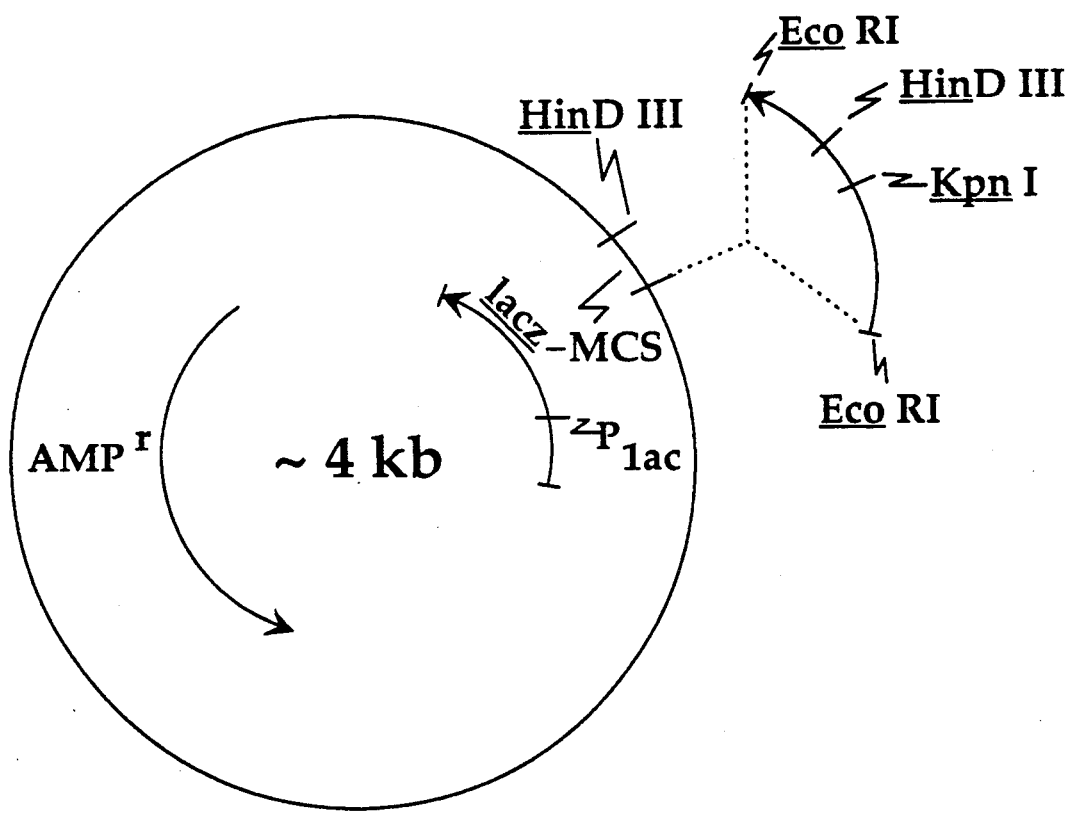
FIG. 3 is a restriction map of the plasmid pUC8.2-14 obtained by inserting a cDNA fragment containing a lipase coding gene from *R. delemar* into pUC8.2 at the Eco RI site.

Insertion of Lipase cDNA Into Plasmid Vector pUC8.2
(see FIG. 3)

The expression vector pUC8.2 was constructed by Hanna et al., [Gene, Vol. 30, (1984), p. 247] from its progenitor plasmid pUC8 [Viera, J. and Messing, J. Gene, Vol. 19, (1982), p. 259]. In pUC8 and pUC8.2 the multiple cloning site, region (MCS, see FIG. 3) is located in the β-galactosidase gene (lac 2' in FIG. 3). In pUC8.2, the phase of the cloning sites in the MCS was shifted while preserving the correct reading frame into the β-galactosidase gene in the construction of pUC8.2 as described by Hanna, et al., (1984), Ibid.. The progenitor pUC8 received two synthetic DNA linker inserts: one insert was at the Eco RI site and shifted the reading frame by one base pair, the other linker insert was at the Hind III site which shifted the reading frame back to the original β-galactosidase gene reading frame, and thereby retained the X-gal (5-bromo-4-chloro-indolyl-β-D-galactoside) screening system of the original pUC8 cloning vector [Viera & Messing, (1982)]. The MCS of pUC8.2 and some flanking β-galactosidase gene sequences are shown in Table 6.

DNA isolated from the recombinant lambda phage R45A4 (EXAMPLE 6) was isolated using standard techniques. This phage DNA was digested with Eco RI endonuclease and ligated to Eco RI-digested pUC8.2 using standard techniques. The ligation mixture was used to transform cells of *E. coli* JM101 [Messing, J., (1979) *Recombinant DNA Technical Bulletin*, NIH Publication No. 79-99, 2, No. 2, p. 43]. Transformants of *E. coli* JM101 synthesizing active lipase were identified on lipase screening agar plates (Table 5) supplemented with ampicillin (100 μg/ml) and IPTG (1 mM) as fluorescent orange colonies when viewed under ultraviolet light (366 nm) illumination. A single lipase-synthesizing transformant of *E. coli* JM101 was picked from the agar plate, grown up in liquid LB medium [Table 5 (b)] supplemented with ampicillin and the plasmid, pUC8.2-14, isolated using standard techniques.

The plasmid pUC8.2-14 was subjected to DNA sequence analysis using the method of Sanger, et al., [Sanger, F., Nicklen S., and Coulson, A. R., Proc. Natl. Acad. Sci. U.S.A., Vol. 74, (1977), p. 5463].

The data confirmed that the 1287 bp Eco RI fragment containing the lipase-encoding sequence was inserted into the Eco RI site of pUC8.2 (Table 6) such that synthesis of lipase is under the transcriptional and translational controls of the β-galactosidase gene. In FIG. 3, the site of insertion of the 1287 bp Eco RI fragment containing the lipase coding sequence (lip) is diagrammed in relation to the MCS, β-galactosidase gene (lac 2'), the promoter of the β-galactosidase gene ($P_{lac}$), and the ampicillin resistance marker of pUC8.2. The approximate location of the unique Kpn I and Hind III endonuclease sites present in the 1287 bp Eco RI fragment are also diagrammed as the expanded insertion arc.

The nucleotide sequence of the cloned cDNA, determined for both strands, is presented in Table 1. Based on the cloning method and vectors used, the upper strand in this Table can be identified as analogous to the mRNA for lipase. Based on the observations of Kozak [Nuclei Acids Res., Vol. 12, (1984), p. 857] the ATG triplet at nucleotides 46–48 is identified as the most probable site of translation initiation. The sequence of the resulting protein, derived by application of the genetic code to the data of Table 1, is presented in Table 2. Within this amino acid sequence, the residues between positions 124 and 151 are identical to the amino terminal 28 residues of the R. delemar lipase (Table 4).

It is concluded that the cloned cDNA contains the sequence for the R. delemar lipase and that this lipase begins at the position 124 serine of the protein encoded by the cloned cDNA, which corresponds to nucleotide 415 of the cloned cDNA (Table 1).

The amino acid composition of the lipase predicted from the cDNA sequence (Table 1, residues 124–392) agrees within accepted experimental error with the composition determined for the purified lipase (Table 3).

The pI of the lipase predicted from the cDNA sequence is identical to that determined in this laboratory for the fungal lipase.

There has been provided in accordance with the present invention, a method for the preparation of recombinant DNA containing a gene coding for lipase enzymes, its incorporation into host microorganisms and the use thereof for the advantages described herein above.

The invention as described by the specific embodiments is not meant to limit its scope. It is envisioned and apparent that many alternatives and variations may be encompassed by the present invention. It is intended that the spirit and scope of this disclosure include such alternatives and variations.

We claim:

1. A recombinant DNA containing a lipase gene comprising a bacteriophage genome having the gene sequence coding for a lipase from Rhizopus delemar (R. delemar) inserted therein.

2. The recombinant DNA of claim 1, wherein said gene sequence consists essentially of the sequence as

TABLE 6 pUC8.2 Plasmid Cloning Vector

Site of Insertion ↓

```
ATG ACC ATG ATT ACG AAT T | GC GAA TTC GC |
TAC TGG TAC TAA TGC TTA A | CG CTT AAG CG |
```

10-mer Eco RI linker

```
         Bam HI              Pst I
A ATT CCC GGG GAT CCG TCG ACC TGC AGC CAA GCT
T TAA GGG CCC CTA GGC AGC TGG ACG TCG GTT CGA
```

Hind III

```
| CCC AAG CTT GGG | AGC TTG
| GGG TTC GAA CCC | TCG AAC
```

12-mer Hind III linker follows:

```
        3        9       15       21       27       33       39       45
  1 GAA TTC CCT TTT CTT CTT ACC CCT TCC AGT TCT TTA CTA TCA ATC
    CTT AAG GGA AAA GAA GAA TGG GGA AGG TCA AGA AAT GAT AGT TAG

46 ATG GTT TCA TTC ATT TCC ATT TCT CAA GGT GTT AGT CTT TGT CTT
    TAC CAA AGT AAG TAA AGG TAA AGA GTT CCA CAA TCA GAA ACA GAA

91 CTT GTC TCT TCC ATG ATG CTC GGT TCA TCT GCT GTT CCT GTT TCT
    GAA CAG AGA AGG TAC TAC GAG CCA AGT AGA CGA CAA GGA CAA AGA

136 GGT AAA TCT GGA TCT TCC AAC ACC GCC GTC TCT GCA TCT GAC AAT
    CCA TTT AGA CCT AGA AGG TTG TGG CGG CAG AGA CGT AGA CTG TTA

181 GCT GCC CTC CCT CCT CTC ATC TCC AGC CGT TGT GCT CCT CCT TCT
    CGA CGG GAG GGA GGA GAG TAG AGG TCG GCA ACA CGA GGA GGA AGA
```

-continued

```
226 AAC AAG GGA AGT AAA AGC GAT CTC CAA GCT GAA CCT TAC AAC ATG
    TTG TTC CCT TCA TTT TCG CTA GAG GTT CGA CTT GGA ATG TTG TAC

271 CAA AAG AAT ACA GAA TGG TAT GAG TCC CAT GGT GGC AAC CTG ACA
    GTT TTC TTA TGT CTT ACC ATA CTC AGG GTA CCA CCG TTG GAC TGT

316 TCC ATC GGA AAG CGT GAT GAC AAC TTG GTT GGT GGC ATG ACT TTG
    AGG TAG CCT TTC GCA CTA CTG TTG AAC CAA CCA CCG TAC TGA AAC

361 GAC TTA CCC AGC GAT GCT CCT CCT ATC AGC CTC TCT AGC TCT ACC
    CTG AAT GGG TCG CTA CGA GGA GGA TAG TCG AGA TCG AGA TGG
```

START OF MATURE FUNGAL PROTEIN
↓

```
406 AAC AGC GCC TCT GAT GGT GGT AAG GTT GTT GCT GCT ACT ACT GCT
    TTG TCG CGG AGA CTA CCA CCA TTC CAA CAA CGA CGA TGA TGA CGA

451 CAG ATC CAA GAG TTC ACC AAG TAT GCT GGT ATC GCT GCC ACT GCC
    GTC TAG GTT CTC AAG TGG TTC ATA CGA CCA TAG CGA CGG TGA CGG

496 TAC TGT CGT TCT GTT GTC CCT GGT AAC AAG TGG GAT TGT GTC CAA
    ATG ACA GCA AGA CAA CAG GGA CCA TTG TTC ACC CTA ACA CAG GTT

541 TGT CAA AAG TGG GTT CCT GAT GGC AAG ATC ATC ACT ACC TTT ACC
    ACA GTT TTC ACC CAA GGA CTA CCG TTG TAG TAG TGA TGG AAA TGG

586 TCC TTG CTT TCC GAT ACA AAT GGT TAC GTC TTG AGA AGT GAT AAA
    AGG AAC GAA AGG CTA TGT TTA CCA ATG CAG AAC TCT TCA CTA TTT

631 CAA AAG ACC ATT TAT CTT GTT TTC CGT GGT ACC AAC TCC TTC AGA
    GTT TTC TGG TAA ATA GAA CAA AAG GCA CCA TGG TTG AGG AAG TCT

676 AGT GCC ATC ACT GAT ATC GTC TTC AAC TTT TCT GAC TAC AAG CCT
    TCA CGG TAG TGA CTA TAG CAG AAG TTG AAA AGA CTG ATG TTC GGA

721 GTC AAG GGC GCC AAA GTT CAT GCT GGT TTC CTT TCC TCT TAT GAG
    CAG TTC CCG CGG TTT CAA GTA CGA CCA AAG GAA AGG AGA ATA CTC

766 CAA GTT GTC AAT GAC TAT TTC CCT GTC GTC CAA GAA CAA TTG ACC
    GTT CAA CAG TTA CTG ATA AAG GGA CAG CAG GTT CTT GTT AAG TGG

811 GCC CAC CCT ACT TAT AAG GTC ATC GTT ACC GGT CAC TCA CTC GGT
    CGG GTG GGA TGA ATA TTC CAG TAG CAA TGG CCA GTG AGT GAG CCA

856 GGT GCA CAA GCT TTG CTT GCC GGT ATG GAT CTC TAC CAA CGT GAA
    CCA CGT GTT CGA AAC GAA CGG CCA TAC CTA GAG ATG GTT GCA CTT

901 CCA AGA TTG TCT CCC AAG AAT TTG AGC ATC TTC ACT GTC GGT GGT
    GGT TCT AAC AGA GGG TTC TTA AAC TCG TAG AAG TGA CAG CCA CCA

946 CCT CGT GTT GGT AAC CCC ACC TTT GCT TAC TAT GTT GAA TCC ACC
    GGA GCA CAA CCA TTG GGG TGG AAA CGA ATG ATA CAA CTT AGG TGG

991 GGT ATC CCT TTC CAA CGT ACC GTT CAC AAG AGA GAT ATC GTT CCT
    CCA TAG GGA AAG GTT GCA TGG CAA GTG TTC TCT CTA TAG CAA GGA

1036 CAC GTT CCT CCT CAA TCC TTC GGA TTC CTT CAT CCC GGT GTT GAA
     GTG CAA GGA GGA GTT AGG AAG CCT AAG GAA GTA GGG CCA CAA CTT

1081 TCT TGG ATC AAG TCT GGT ACT TCC AAC GTT CAA ATC TGT ACT TCT
     AGA ACC TAG TTC AGA CCA TGA AGG TTG CAA GTT TAG ACA TGA AGA

1126 GAA ATT GAA ACC AAG GAT TGC AGT AAC TCT ATC GTT CCT TTC ACC
     CTT TAA CTT TGG TTC CTA ACG TCA TTG AGA TAG CAA GGA AAG TGG

1171 TCT ATC CTT GAC CAC TTG AGT TAC TTT GAT ATC AAC GAA GGA AGC
     AGA TAG GAA CTG GTG AAC TCA ATG AAA CTA TAG TTG CTT CCT TCG

1216 TGT TTG TAA AAC ACT TGA CGT GTT ACT CTA ATT TTA TAA TAA AAT
     ACA AAC ATT TTG TGA ACT GCA CAA TGA GAT TAA ATT ATT ATT TTA

1261 TAA GTT TTT ATA CAA TAA AAG GAA TTC
     ATT CAA AAA TAT GTT ATT TTC CTT AAG
```

3. A microorganism containing a bacteriophage having the gene sequence coding for lipase from *R. delemar*.

4. The microorganism of claim 3, wherein said gene sequence consists essentially of the sequence as follows:

```
              3           9          15          21          27          33          39          45
  1 GAA TTC CCT TTT CTT CTT ACC CCT TCC AGT TCT TTA CTA TCA ATC
    CTT AAG GGA AAA GAA GAA TGG GGA AGG TCA AGA AAT GAT AGT TAG

46 ATG GTT TCA TTC ATT TCC ATT TCT CAA GGT GTT AGT CTT TGT CTT
    TAC CAA AGT AAG TAA AGG TAA AGA GTT CCA CAA TCA GAA ACA GAA

91 CTT GTC TCT TCC ATG ATG CTC GGT TCA TCT GCT GTT CCT GTT TCT
    GAA CAG AGA AGG TAC TAC GAG CCA AGT AGA CGA CAA GGA CAA AGA

136 GGT AAA TCT GGA TCT TCC AAC ACC GCC GTC TCT GCA TCT GAC AAT
    CCA TTT AGA CCT AGA AGG TTG TGG CGG CAG AGA CGT AGA CTG TTA

181 GCT GCC CTC CCT CCT CTC ATC TCC AGC CGT TGT GCT CCT CCT TCT
    CGA CGG GAG GGA GGA GAG TAG AGG TCG GCA ACA CGA GGA GGA AGA

226 AAC AAG GGA AGT AAA AGC GAT CTC CAA GCT GAA CCT TAC AAC ATG
    TTG TTC CCT TCA TTT TCG CTA GAG GTT CGA CTT GGA ATG TTG TAC

271 CAA AAG AAT ACA GAA TGG TAT GAG TCC CAT GGT GGC AAC CTG ACA
    GTT TTC TTA TGT CTT ACC ATA CTC AGG GTA CCA CCG TTG GAC TGT

316 TCC ATC GGA AAG CGT GAT GAC AAC TTG GTT GGT GGC ATG ACT TTG
    AGG TAG CCT TTC GCA CTA CTG TTG AAC CAA CCA CCG TAC TGA AAC

361 GAC TTA CCC AGC GAT GCT CCT CCT ATC AGC CTC TCT AGC TCT ACC
    CTG AAT GGG TCG CTA CGA GGA GGA TAG TCG GAG AGA TCG AGA TGG
                   START OF MATURE FUNGAL PROTEIN
```
```
406 AAC AGC GCC TCT GAT GGT GGT AAG GTT GTT GCT GCT ACT ACT GCT
    TTG TCG CGG AGA CTA CCA CCA TTC CAA CAA CGA CGA TGA TGA CGA 451 CAG ATC CAA GAG TTC ACC AAG TAT GCT GGT ATC GCT GCC ACT GCC
    GTC TAG GTT CTC AAG TGG TTC ATA CGA CCA TAG CGA CGG TGA CGG 496 TAC TGT CGT TCT GTT GTC CCT GGT AAC AAG TGG GAT TGT GTC CAA
    ATG ACA GCA AGA CAA CAG GGA CCA TTG TTC ACC CTA ACA CAG GTT 541 TGT CAA AAG TGG GTT CCT GAT GGC AAG ATC ATC ACT ACC TTT ACC
    ACA GTT TTC ACC CAA GGA CTA CCG TTG TAG TAG TGA TGG AAA TGG 586 TCC TTG CTT TCC GAT ACA AAT GGT TAC GTC TTG AGA AGT GAT AAA
    AGG AAC GAA AGG CTA TGT TTA CCA ATG CAG AAC TCT TCA CTA TTT 631 CAA AAG ACC ATT TAT CTT GTT TTC CGT GGT ACC AAC TCC TTC AGA
    GTT TTC TGG TAA ATA GAA CAA AAG GCA CCA TGG TTG AGG AAG TCT 676 AGT GCC ATC ACT GAT ATC GTC TTC AAC TTT TCT GAC TAC AAG CCT
    TCA CGG TAG TGA CTA TAG CAG AAG TTG AAA AGA CTG ATG TTC GGA 721 GTC AAG GGC GCC AAA GTT CAT GCT GGT TTC CTT TCC TCT TAT GAG
    CAG TTC CCG CGG TTT CAA GTA CGA CCA AAG GAA AGG AGA ATA CTC 766 CAA GTT GTC AAT GAC TAT TTC CCT GTC GTC CAA GAA CAA TTG ACC
    GTT CAA CAG TTA CTG ATA AAG GGA CAG CAG GTT CTT GTT AAC TGG 811 GCC CAC CCT ACT TAT AAG GTC ATC GTT ACC GGT CAC TCA CTC GGT
    CGG GTG GGA TGA ATA TTC CAG TAG CAA TGG CCA GTG AGT GAG CCA 856 GGT GCA CAA GCT TTG CTT GCC GGT ATG GAT CTC TAC CAA CGT GAA
    CCA CGT GTT CGA AAC GAA CGG CCA TAC CTA GAG ATG GTT GCA CTT 901 CCA AGA TTG TCT CCC AAG AAT TTG AGC ATC TTC ACT GTC GGT GGT
    GGT TCT AAC AGA GGG TTC TTA AAC TCG TAG AAG TGA CAG CCA CCA 946 CCT CGT GTT GGT AAC CCC ACC TTT GCT TAC TAT GTT GAA TCC ACC
    GGA GCA CAA CCA TTG GGG TGG AAA CGA ATG ATA CAA CTT AGG TGG 991 GGT ATC CCT TTC CAA CGT ACC GTT CAC AAG AGA GAT ATC GTT CCT
    CCA TAG GGA AAG GTT GCA TGG CAA GTG TTC TCT CTA TAG CAA GGA 1036 CAC GTT CCT CCT CAA TCC TTC GGA TTC CTT CAT CCC GGT GTT GAA
     GTG CAA GGA GGA GTT AGG AAG CCT AAG GAA GTA GGG CCA CAA CTT 1081 TCT TGG ATC AAG TCT GGT ACT TCC AAC GTT CAA ATC TGT ACT TCT
     AGA ACC TAG TTC AGA CCA TGA AGG TTG CAA GTT TAG ACA TGA AGA 1126 GAA ATT GAA ACC AAG GAT TGC AGT AAC TCT ATC GTT CCT TTC ACC
     CTT TAA CTT TGG TTC CTA ACG TCA TTG AGA TAG CAA GGA AAG TGG
```

-continued

```
1171 TCT ATC CTT GAC CAC TTG AGT TAC TTT GAT ATC AAC GAA GGA AGC
    AGA TAG GAA CTG GTG AAC TCA ATG AAA CTA TAG TTG CTT CCT TCG

1216 TGT TTG TAA AAC ACT TGA CGT GTT ACT CTA ATT TTA TAA TAA AAT
    ACA AAC ATT TTG TGA ACT GCA CAA TGA GAT TAA AAT ATT ATT TTA

1261 TAA GTT TTT ATA CAA TAA AAG GAA TTC
    ATT CAA AAA TAT GTT ATT TTC CTT AAG
```

5. The microorganism of claim 3, wherein said microorganism is *E. coli*.

6. The microorganism of claim 4, wherein said microorganism is *E. coli*.

7. A biologically pure culture of a microorganism characterized in that its cells contain a plasmid with a gene sequence encoding a lipase from *R. delmar*.

8. The biologically pure culture of claim 7, wherein the cells express lipase.

9. The biologically pure culture of claim 8, wherein said microorganism is *E. coli*.

10. The biologically pure culture of claim 7, wherein said microorganism is *E. coli*.

11. The biologically pure culture of claim 9, wherein said gene sequence consists essentially of the sequence as follows:

```
         3         9        15        21        27        33        39        45
  1 GAA TTC CCT TTT CTT CTT ACC CCT TCC AGT TCT TTA CTA TCA ATC
    CTT AAG GGA AAA GAA GAA TGG GGA AGG TCA AGA AAT GAT AGT TAG

46 ATG GTT TCA TTC ATT TCC ATT TCT CAA GGT GTT AGT CTT TGT CTT
    TAC CAA AGT AAG TAA AGG TAA AGA GTT CCA CAA TCA GAA ACA GAA

91 CTT GTC TCT TCC ATG ATG CTC GGT TCA TCT GCT GTT CCT GTT TCT
    GAA CAG AGA AGG TAC TAC GAG CCA AGT AGA CGA CAA GGA CAA AGA

136 GGT AAA TCT GGA TCT TCC AAC ACC GCC GTC TCT GCA TCT GAC AAT
    CCA TTT AGA CCT AGA AGG TTG TGG CGG CAG AGA CGT AGA CTG TTA

181 GCT GCC CTC CCT CCT CTC ATC TCC AGC CGT TGT GCT CCT CCT TCT
    CGA CGG GAG GGA GGA GAG TAG AGG TCG GCA ACA CGA GGA GGA AGA

226 AAC AAG GGA AGT AAA AGC GAT CTC CAA GCT GAA CCT TAC AAC ATG
    TTG TTC CCT TCA TTT TCG CTA GAG GTT CGA CTT GGA ATG TTG TAC

271 CAA AAG AAT ACA GAA TGG TAT GAG TCC CAT GGT GGC AAC CTG ACA
    GTT TTC TTA TGT CTT ACC ATA CTC AGG GTA CCA CCG TTG GAC TGT

316 TCC ATC GGA AAG CGT GAT GAC AAC TTG GTT GGT GGC ATG ACT TTG
    AGG TAG CCT TTC GCA CTA CTG TTG AAC CAA CCA CCG TAC TGA AAG

361 GAC TTA CCC AGC GAT GCT CCT CCT ATC AGC CTC TCT AGC TCT ACC
    CTG AAT GGG TCG CTA CGA GGA GGA TAG TCG GAG AGA TCG AGA TGG
```

START OF MATURE FUNGAL PROTEIN

```
406 AAC AGC GCC TCT GAT GGT GGT AAG GTT GTT GCT GCT ACT ACT GCT
    TTG TCG CGG AGA CTA CCA CCA TTC CAA CAA CGA CGA TGA TGA CGA

451 CAG ATC CAA GAG TTC ACC AAG TAT GCT GGT ATC GCT GCC ACT GCC
    GTC TAG GTT CTC AAG TGG TTC ATA CGA CCA TAG CGA CGG TGA CGG

496 TAC TGT CGT TCT GTT GTC CCT GGT AAC AAG TGG GAT TGT GTC CAA
    ATG ACA GCA AGA CAA CAG GGA CCA TTG TTC ACC CTA ACA CAG GTT

541 TGT CAA AAG TGG GTT CCT GAT GGC AAG ATC ATC ACT ACC TTT ACC
    ACA GTT TTC ACC CAA GGA CTA CCG TTG TAG TAG TGA TGG AAA TGG

586 TCC TTG CTT TCC GAT ACA AAT GGT TAC GTC TTG AGA AGT GAT AAA
    AGG AAC GAA AGG CTA TGT TTA CCA ATG CAG AAC TCT TCA CTA TTT

631 CAA AAG ACC ATT TAT CTT GTT TTC CGT GGT ACC AAC TCC TTC AGA
    GTT TTC TGG TAA ATA GAA CAA AAG GCA CCA TGG TTG AGG AAG TCT

676 AGT GCC ATC ACT GAT ATC GTC TTC AAC TTT TCT GAC TAC AAG CCT
    TCA CGG TAG TGA CTA TAG CAG AAG TTG AAA AGA CTG ATG TTC GGA

721 GTC AAG GGC GCC AAA GTT CAT GCT GGT TTC CTT TCC TCT TAT GAG
    CAG TTC CCG CGG TTT CAA GTA CGA CCA AAG GAA AGG AGA ATA CTC

766 CAA GTT GTC AAT GAC TAT TTC CCT GTC GTC CAA GAA CAA TTG ACC
    GTT CAA CAG TTA CTG ATA AAG GGA CAG CAG GTT CTT GTT AAC TGG
```

```
 811 GCC CAC CCT ACT TAT AAG GTC ATC GTT ACC GGT CAC TCA CTC GGT
     CGG GTG GGA TGA ATA TTC CAG TAG CAA TGG CCA GTG AGT GAG CCA

856 GGT GCA CAA GCT TTG CTT GCC GGT ATG GAT CTC TAC CAA CGT GAA
     CCA CGT GTT CGA AAC GAA CGG CCA TAC CTA GAG ATG GTT GCA CTT

901 CCA AGA TTG TCT CCC AAG AAT TTG AGC ATC TTC ACT GTC GGT GGT
     GGT TCT AAC AGA GGG TTC TTA AAC TCG TAG AAG TGA CAG CCA CCA

946 CCT CGT GTT GGT AAC CCC ACC TTT GCT TAC TAT GTT GAA TCC ACC
     GGA GCA CAA CCA TTG GGG TGG AAA CGA ATG ATA CAA CTT AGG TGG

991 GGT ATC CCT TTC CAA CGT ACC GTT CAC AAG AGA GAT ATC GTT CCT
     CCA TAG GGA AAG GTT GCA TGG CAA GTG TTC TCT CTA TAG CAA GGA

1036 CAC GTT CCT CCT CAA TCC TTC GGA TTC CTT CAT CCC GGT GTT GAA
     GTG CAA GGA GGA GTT AGG AAG CCT AAG GAA GTA GGG CCA CAA CTT

1081 TCT TGG ATC AAG TCT GGT ACT TCC AAC GTT CAA ATC TGT ACT TCT
     AGA ACC TAG TTC AGA CCA TGA AGG TTG CAA GTT TAG ACA TGA AGA

1126 GAA ATT GAA ACC AAG GAT TGC AGT AAC TCT ATC GTT CCT TTC ACC
     CTT TAA CTT TGG TTC CTA ACG TCA TTG AGA TAG CAA GGA AAG TGG

1171 TCT ATC CTT GAC CAC TTG AGT TAC TTT GAT ATC AAC GAA GGA AGC
     AGA TAG GAA CTG GTG AAC TCA ATG AAA CTA TAG TTG CTT CCT TCG

1216 TGT TTG TAA AAC ACT TGA CGT GTT ACT CTA ATT TTA TAA TAA AAT
     ACA AAC ATT TTG TGA ACT GCA CAA TGA GAT TAA AAT ATT ATT TTA

1261 TAA GTT TTT ATA CAA TAA AAG GAA TTC
     ATT CAA AAA TAT GTT ATT TTC CTT AAG
```

12. The biologically pure culture of claim 10, wherein said gene sequence consists essentially of the sequence as follows:

```
       3         9        15        21        27        33        39        45
  1 GAA TTC CCT TTT CTT CTT ACC CCT TCC AGT TCT TTA CTA TCA ATC
    CTT AAG GGA AAA GAA GAA TGG GGA AGG TCA AGA AAT GAT AGT TAG

46 ATG GTT TCA TTC ATT TCC ATT TCT CAA GGT GTT AGT CTT TGT CTT
    TAC CAA AGT AAG TAA AGG TAA AGA GTT CCA CAA TCA GAA ACA GAA

91 CTT GTC TCT TCC ATG ATG CTC GGT TCA TCT GCT GTT CCT GTT TCT
    GAA CAG AGA AGG TAC TAC GAG CCA AGT AGA CGA CAA GGA CAA AGA

136 GGT AAA TCT GGA TCT TCC AAC ACC GCC GTC TCT GCA TCT GAC AAT
    CCA TTT AGA CCT AGA AGG TTG TGG CGG CAG AGA CGT AGA CTG TTA

181 GCT GCC CTC CCT CCT CTC ATC TCC AGC CGT TGT GCT CCT CCT TCT
    CGA CGG GAG GGA GGA GAG TAG AGG TCG GCA ACA CGA GGA GGA AGA

226 AAC AAG GGA AGT AAA AGC GAT CTC CAA GCT GAA CCT TAC AAC ATG
    TTG TTC CCT TCA TTT TCG CTA GAG GTT CGA CTT GGA ATG TTG TAC

271 CAA AAG AAT ACA GAA TGG TAT GAG TCC CAT GGT GGC AAC CTG ACA
    GTT TTC TTA TGT CTT ACC ATA CTC AGG GTA CCA CCG TTG GAC TGT

316 TCC ATC GGA AAG CGT GAT GAC AAC TTG GTT GGT GGC ATG ACT TTG
    AGG TAG CCT TTC GCA CTA CTG TTG AAC CAA CCA CCG TAC TGA AAG

361 GAC TTA CCC AGC GAT GCT CCT CCT ATC AGC CTC TCT AGC TCT ACC
    CTG AAT GGG TCG CTA CGA GGA GGA TAG TCG AGA GAT CGA GAT GG
```

START OF MATURE FUNGAL PROTEIN

```
406 AAC AGC GCC TCT GAT GGT GGT AAG GTT GTT GCT GCT ACT ACT GCT
    TTG TCG CGG AGA CTA CCA CCA TTC CAA CAA CGA CGA TGA TGA CGA

451 CAG ATC CAA GAG TTC ACC AAG TAT GCT GGT ATC GCT GCC ACT GCC
    GTC TAG GTT CTC AAG TGG TTC ATA CGA CCA TAG CGA CGG TGA CGG

496 TAC TGT CGT TCT GTT GTC CCT GGT AAC AAG TGG GAT TGT GTC CAA
    ATG ACA GCA AGA CAA CAG GGA CCA TTG TTC ACC CTA ACA CAG GTT

541 TGT CAA AAG TGG GTT CCT GAT GGC AAG ATC ATC ACT ACC TTT ACC
    ACA GTT TTC ACC CAA GGA CTA CCG TTG TAG TAG TGA TGG AAA TGG
```

```
586 TCC TTG CTT TCC GAT ACA AAT GGT TAC GTC TTG AGA AGT GAT AAA
    AGG AAC GAA AGG CTA TGT TTA CCA ATG CAG AAC TCT TCA CTA TTT

631 CAA AAG ACC ATT TAT CTT GTT TTC CGT GGT ACC AAC TCC TTC AGA
    GTT TTC TGG TAA ATA GAA CAA AAG GCA CCA TGG TTG AGG AAG TCT

676 AGT GCC ATC ACT GAT ATC GTC TTC AAC TTT TCT GAC TAC AAG CCT
    TCA CGG TAG TAG CTA TAG CAG AAG TTG AAA AGA CTG ATG TTC GGA

721 GTC AAG GGC GCC AAA GTT CAT GCT GGT TTC CTT TCC TCT TAT GAG
    CAG TTC CCG CGG TTT CAA GTA CGA CCA AAG GAA AGG AGA ATA CTC

766 CAA GTT GTC AAT GAC TAT TTC CCT GTC GTC CAA GAA CAA TTG ACC
    GTT CAA CAG TTA CTG ATA AAG GGA CAG CAG GTT CTT GTT AAC TGG

811 GCC CAC CCT ACT TAT AAG GTC ATC GTT ACC GGT CAC TCA CTC GGT
    CGG GTG GGA TGA ATA TTC CAG TAG CAA TGG CCA GTG AGT GAG CCA

856 GGT GCA CAA GCT TTG CTT GCC GGT ATG GAT CTC TAC CAA CGT GAA
    CCA CGT GTT CGA AAC GAA CGG CCA TAC CTA GAG ATG GTT GCA CTT

901 CCA AGA TTG TCT CCC AAG AAT TTG AGC ATC TTC ACT GTC GGT GGT
    GGT TCT AAC AGA GGG TTC TTA AAC TCG TAG AAG TGA CAG CCA CCA

946 CCT CGT GTT GGT AAC CCC ACC TTT GCT TAC TAT GTT GAA TCC ACC
    GGA GCA CAA CCA TTG GGG TGG AAA CGA ATG ATA CAA CTT AGG TGG

991 GGT ATC CCT TTC CAA CGT ACC GTT CAC AAG AGA GAT ATC GTT CCT
    CCA TAG GGA AAG GTT GCA TGG CAA GTG TTC TCT CTA TAG CAA GGA

1036 CAC GTT CCT CCT CAA TCC TTC GGA TTC CTT CAT CCC GGT GTT GAA
     GTG CAA GGA GGA GTT AGG AAG CCT AAG GAA GTA GGG CCA CAA CTT

1081 TCT TGG ATC AAG TCT GGT ACT TCC AAC GTT CAA ATC TGT ACT TCT
     AGA ACC TAG TTC AGA CCA TGA AGG TTG CAA GTT TAG ACA TGA AGA

1126 GAA ATT GAA ACC AAG GAT TGC AGT AAC TCT ATC GTT CCT TTC ACC
     CTT TAA CTT TGG TTC CTA ACG TCA TTG AGA TAG CAA GGA AAG TGG

1171 TCT ATC CTT GAC CAC TTG AGT TAC TTT GAT ATC AAC GAA GGA AGC
     AGA TAG GAA CTG GTG AAC TCA ATG AAA CTA TAG TTG CTT CCT TCG

1216 TGT TTG TAA AAC ACT TGA CGT GTT ACT CTA ATT TTA TAA TAA AAT
     ACA AAC ATT TTG TGA ACT GCA CAA TGA GAT TAA AAT ATT ATT TTA

1261 TAA GTT TTT ATA CAA TAA AAG GAA TTC
     ATT CAA AAA TAT GTT ATT TTC CTT AAG
```

13. A recombinant plasmid comprising a vector and a cDNA sequence for a lipase from *R. delemar*.

14. The recombinant plasmid of claim 13, wherein said cDNA sequence consists essentially of the sequence as follows:

```
                3     9     15    21    27    33    39    45
  1 GAA TTC CCT TTT CTT CTT ACC CCT TCC AGT TCT TTA CTA TCA ATC
    CTT AAG GGA AAA GAA GAA TGG GGA AGG TCA AGA AAT GAT AGT TAG

46 ATG GTT TCA TTC ATT TCC ATT TCT CAA GGT GTT AGT CTT TGT CTT
    TAC CAA AGT AAG TAA AGG TAA AGA GTT CCA CAA TCA GAA ACA GAA

91 CTT GTC TCT TCC ATG ATG CTC GGT TCA TCT GCT GTT CCT GTT TCT
    GAA CAG AGA AGG TAC TAC GAG CCA AGT AGA CGA CAA GGA CAA AGA

136 GGT AAA TCT GGA TCT TCC AAC ACC GCC GTC TCT GCA TCT GAC AAT
    CCA TTT AGA CCT AGA AGG TTG TGG CGG CAG AGA CGT AGA CTG TTA

181 GCT GCC CTC CCT CCT CTC ATC TCC AGC CGT TGT GCT CCT CCT TCT
    CGA CGG GAG GGA GGA GAG TAG AGG TCG GCA ACA CGA GGA GGA AGA

226 AAC AAG GGA AGT AAA AGC GAT CTC CAA GCT GAA CCT TAC AAC ATG
    TTG TTC CCT TCA TTT TCG CTA GAG GTT CGA CTT GGA ATG TTG TAC

271 CAA AAG AAT ACA GAA TGG TAT GAG TCC CAT GGT GGC AAC CTG ACA
    GTT TTC TTA TGT CTT ACC ATA CTC AGG GTA CCA CCG TTG GAC TGT

316 TCC ATC GGA AAG CGT GAT GAC AAC TTG GTT GGT GGC ATG ACT TTG
    AGG TAG CCT TTC GCA CTA CTG TTG AAC CAA CCA CCG TAC TGA AAC

361 GAC TTA CCC AGC GAT GCT CCT CCT ATC AGC CTC TCT AGC TCT ACC
    CTG AAT GGG TCG CTA CGA GGA GGA TAG TCG GAG AGA TCG AGA TGG
```

START OF MATURE FUNGAL PROTEIN

```
 406 AAC AGC GCC TCT GAT GGT GGT AAG GTT GTT GCT GCT ACT ACT GCT
     TTG TCG CGG AGA CTA CCA CCA TTC CAA CAA CGA CGA TGA TGA CGA

451 CAG ATC CAA GAG TTC ACC AAG TAT GCT GGT ATC GCT GCC ACT GCC
     GTC TAG GTT CTC AAG TGG TTC ATA CGA CCA TAG CGA CGG TGA CGG

496 TAC TGT CGT TCT GTT GTC CCT GGT AAC AAG TGG GAT TGT GTC CAA
     ATG ACA GCA AGA CAA CAG GGA CCA TTG TTC ACC CTA ACA CAG GTT

541 TGT CAA AAG TGG GTT CCT GAT GGC AAG ATC ATC ACT ACC TTT ACC
     ACA GTT TTC ACC CAA GGA CTA CCG TTG TAG TAG TGA TGG AAA TGG

586 TCC TTG CTT TCC GAT ACA AAT GGT TAC GTC TTG AGA AGT GAT AAA
     AGG AAC GAA AGG CTA TGT TTA CCA ATG CAG AAC TCT TCA CTA TTT

631 CAA AAG ACC ATT TAT CTT GTT TTC CGT GGT ACC AAC TCC TTC AGA
     GTT TTC TGG TAA ATA GAA CAA AAG GCA CCA TGG TTG AGG AAG TCT

676 AGT GCC ATC ACT GAT ATC GTC TTC AAC TTT TCT GAC TAC AAG CCT
     TCA CGG TAG TGA CTA TAG CAG AAG TTG AAA AGA CTG ATG TTC GGA

721 GTC AAG GGC GCC AAA GTT CAT GCT GGT TTC CTT TCC TCT TAT GAG
     CAG TTC CCG CGG TTT CAA GTA CGA CCA AAG GAA AGG AGA ATA CTC

766 CAA GTT GTC AAT GAC TAT TTC CCT GTC GTC CAA GAA CAA TTG ACC
     GTT CAA CAG TTA CTG ATA AAG GGA CAG CAG GTT CTT GTT AAC TGG

811 GCC CAC CCT ACT TAT AAG GTC ATC GTT ACC GGT CAC TCA CTC GGT
     CGG GTG GGA TGA ATA TTC CAG TAG CAA TGG CCA GTG AGT GAG CCA

856 GGT GCA CAA GCT TTG CTT GCC GGT ATG GAT CTC TAC CAA CGT GAA
     CCA CGT GTT CGA AAC GAA CGG CCA TAC CTA GAG ATG GTT GCA CTT

901 CCA AGA TTG TCT CCC AAG AAT TTG AGC ATC TTC ACT GTC GGT GGT
     GGT TCT AAC AGA GGG TTC TTA AAC TCG TAG AAG TGA CAG CCA CCA

946 CCT CGT GTT GGT AAC CCC ACC TTT GCT TAC TAT GTT GAA TCC ACC
     GGA GCA CAA CCA TTG GGG TGG AAA CGA ATG ATA CAA CTT AGG TGG

991 GGT ATC CCT TTC CAA CGT ACC GTT CAC AAG AGA GAT ATC GTT CCT
     CCA TAG GGA AAG GTT GCA TGG CAA GTG TTC TCT CTA TAG CAA GGA

1036 CAC GTT CCT CCT CAA TCC TTC GGA TTC CTT CAT CCC GGT GTT GAA
     GTG CAA GGA GGA GTT AGG AAG CCT AAG GAA GTA GGG CCA CAA CTT

1081 TCT TGG ATC AAG TCT GGT ACT TCC AAC GTT CAA ATC TGT ACT TCT
     AGA ACC TAG TTC AGA CCA TGA AGG TTG CAA GTT TAG ACA TGA AGA

1126 GAA ATT GAA ACC AAG GAT TGC AGT AAC TCT ATC GTT CCT TTC ACC
     CTT TAA CTT TGG TTC CTA ACG TCA TTG AGA TAG CAA GGA AAG TGG

1171 TCT ATC CTT GAC CAC TTG AGT TAC TTT GAT ATC AAC GAA GGA AGC
     AGA TAG GAA CTG GTG AAC TCA ATG AAA CTA TAG TTG CTT CCT TCG

1216 TGT TTG TAA AAC ACT TGA CGT GTT ACT CTA ATT TTA TAA TAA AAT
     ACA AAC ATT TTG TGA ACT GCA CAA TGA GAT TAA AAT ATT ATT TTA

1261 TAA GTT TTT ATA CAA TAA AAG GAA TTC
     ATT CAA AAA TAT GTT ATT TTC CTT AAG
```

15. A recombinant plasmid comprising the gene sequence as follows:

Site of Insertion

```
ATG ACC ATG ATT ACG AAT T | GC GAA TTC GC |
TAC TGG TAC TAA TGC TTA A | CG CTT AAG CG |
                           10-mer Eco RI linker
```

```
     Bam HI                  Pst I

A ATT CCC GGG GAT CCG TCG ACC TGC AGC CAA GCT
T TAA GGG CCC CTA GGC AGC TGC ACG TCG GTT CGA
```

```
        Hind III
| CCC AAG CTT GGG | AGC TTG
| GGG TTC GAA CCC | TCG AAC 12-mer Hind III linker
``` having inserted therein at the Eco RI site a gene sequence coding lipase from *R. delemar.*

16. The plasmid of claim 15, wherein said gene sequence coding for a lipase consists essentially of the sequence as follows:

```
          3         9        15        21        27        33        39        45
  1 GAA TTC CCT TTT CTT CTT ACC CCT TCC AGT TCT TTA CTA TCA ATC
    CTT AAG GGA AAA GAA GAA TGG GGA AGG TCA AGA AAT GAT AGT TAG

46 ATG GTT TCA TTC ATT TCC ATT TCT CAA GGT GTT AGT CTT TGT CTT
    TAC CAA AGT AAG TAA AGG TAA AGA GTT CCA CAA TCA GAA ACA GAA

91 CTT GTC TCT TCC ATG ATG CTC GGT TCA TCT GCT GTT CCT GTT TCT
    GAA CAG AGA AGG TAC TAC GAG CCA AGT AGA CGA CAA GGA CAA AGA

136 GGT AAA TCT GGA TCT TCC AAC ACC GCC GTC TCT GCA TCT GAC AAT
    CCA TTT AGA CCT AGA AGG TTG TGG CGG CAG AGA CGT AGA CTG TTA

181 GCT GCC CTC CCT CCT CTC ATC TCC AGC CGT TGT GCT CCT CCT TCT
    CGA CGG GAG GGA GGA GAG TAG AGG TCG GCA ACA CGA GGA GGA AGA

226 AAC AAG GGA AGT AAA AGC GAT CTC CAA GCT GAA CCT TAC AAC ATG
    TTG TTC CCT TCA TTT TCG CTA GAG GTT CGA CTT GGA ATG TTG TAC

271 CAA AAG AAT ACA GAA TGG TAT GAG TCC CAT GGT GGC AAC CTG ACA
    GTT TTC TTA TGT CTT ACC ATA CTC AGG GTA CCA CCG TTG GAC TGT

316 TCC ATC GGA AAG CGT GAT GAC AAC TTG GTT GGT GGC ATG ACT TTG
    AGG TAG CCT TTC GCA CTA CTG TTG AAC CAA CCA CCG TAC TGA AAG

361 GAC TTA CCC AGC GAT GCT CCT CCT ATC AGC CTC TCT AGC TCT ACC
    CTG AAT GGG TCG CTA CGA GGA GGA TAG TCG GAG AGA TCG AGA TGG

START OF MATURE FUNGAL PROTEIN
```
```
406 AAC AGC GCC TCT GAT GGT GGT AAG GTT GTT GCT GCT ACT ACT GCT
    TTG TCG CGG AGA CTA CCA CCA TTC CAA CAA CGA CGA TGA TGA CGA 451 CAG ATC CAA GAG TTC ACC AAG TAT GCT GGT ATC GCT GCC ACT GCC
    GTC TAG GTT CTC AAG TGG TTC ATA CGA CCA TAG CGA CGG TGA CGG 496 TAC TGT CGT TCT GTT GTC CCT GGT AAC AAG TGG GAT TGT GTC CAA
    ATG ACA GCA AGA CAA CAG GGA CCA TTG TTC ACC CTA ACA CAG GTT 541 TGT CAA AAG TGG GTT CCT GAT GGC AAG ATC ATC ACT ACC TTT ACC
    ACA GTT TTC ACC CAA GGA CTA CCG TTG TAG TAG TGA TGG AAA TGG 586 TCC TTG CTT TCC GAT ACA AAT GGT TAC GTC TTG AGA AGT GAT AAA
    AGG AAC GAA AGG CTA TGT TTA CCA ATG CAG AAC TCT TCA CTA TTT 631 CAA AAG ACC ATT TAT CTT GTT TTC CGT GGT ACC AAC TCC TTC AGA
    GTT TTC TGG TAA ATA GAA CAA AAG GCA CCA TGG TTG AGG AAG TCT 676 AGT GCC ATC ACT GAT ATC GTC TTC AAC TTT TCT GAC TAC AAG CCT
    TCA CGG TAG TGA CTA TAG CAG AAG TTG AAA AGA CTG ATG TTC GGA 721 GTC AAG GGC GCC AAA GTT CAT GCT GGT TTC CTT TCC TCT TAT GAG
    CAG TTC CCG CGG TTT CAA GTA CGA CCA AAG GAA AGG AGA ATA CTC 766 CAA GTT GTC AAT GAC TAT TTC CCT GTC GTC CAA GAA CAA TTG ACC
    GTT CAA CAG TTA CTG ATA AAG GGA CAG CAG GTT CTT GTT AAC TGG 811 GCC CAC CCT ACT TAT AAG GTC ATC GTT ACC GGT CAC TCA CTC GGT
    CGG GTG GGA TGA ATA TTC CAG TAG CAA TGG CCA GTG AGT GAG CCA 856 GGT GCA CAA GCT TTG CTT GCC GGT ATG GAT CTC TAC CAA CGT GAA
    CCA CGT GTT CGA AAC GAA CGG CCA TAC CTA GAG ATG GTT GCA CTT 901 CCA AGA TTG TCT CCC AAG AAT TTG AGC ATC TTC ACT GTC GGT GGT
    GGT TCT AAC AGA GGG TTC TTA AAC TCG TAG AAG TGA CAG CCA CCA 946 CCT CGT GTT GGT AAC CCC ACC TTT GCT TAC TAT GTT GAA TCC ACC
    GGA GCA CAA CCA TTG GGG TGG AAA CGA ATG ATA CAA CTT AGG TGG
```

-continued

```
 991 GGT ATC CCT TTC CAA CGT ACC GTT CAC AAG AGA GAT ATC GTT CCT
     CCA TAG GGA AAG GTT GCA TGG CAA GTG TTC TCT CTA TAG CAA GGA

1036 CAC GTT CCT CCT CAA TCC TTC GGA TTC CTT CAT CCC GGT GTT GAA
     GTG CAA GGA GGA GTT AGG AAG CCT AAG GAA GTA GGG CCA CAA CTT

1081 TCT TGG ATC AAG TCT GGT ACT TCC AAC GTT CAA ATC TGT ACT TCT
     AGA ACC TAG TTC AGA CCA TGA AGG TTG CAA GTT TAG ACA TGA AGA

1126 GAA ATT GAA ACC AAG GAT TGC AGT AAC TCT ATC GTT CCT TTC ACC
     CTT TAA CTT TGG TTC CTA ACG TCA TTG AGA TAG CAA GGA AAG TGG

1171 TCT ATC CTT GAC CAC TTG AGT TAC TTT GAT ATC AAC GAA GGA AGC
     AGA TAG GAA CTG GTG AAC TCA ATG AAA CTA TAG TTG CTT CCT TCG

1216 TGT TTG TAA AAC ACT TGA CGT GTT ACT CTA ATT TTA TAA TAA AAT
     ACA AAC ATT TTG TGA ACT GCA CAA TGA GAT TAA AAT ATT ATT TTA

1261 TAA GTT TTT ATA CAA TAA AAG GAA TTC
     ATT CAA AAA TAT GTT ATT TTC CTT AAG
```

17. The recombinant DNA of claim 1, wherein said bacteriophage genome is a bacteriophage lambda genome.

18. The microorganism of claim 3, wherein said bacteriophage is a lambda bacteriophage.

* * * * *